United States Patent
Nakaya et al.

(10) Patent No.: US 10,174,434 B2
(45) Date of Patent: Jan. 8, 2019

(54) PLATING SOLUTION USING PHOSPHONIUM SALT

(71) Applicant: MITSUBISHI MATERIALS CORPORATION, Tokyo (JP)

(72) Inventors: Kiyotaka Nakaya, Naka-shi (JP); Mami Watanabe, Naka (JP)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 0 days.

(21) Appl. No.: 15/560,629

(22) PCT Filed: Mar. 24, 2016

(86) PCT No.: PCT/JP2016/059424
§ 371 (c)(1),
(2) Date: Sep. 22, 2017

(87) PCT Pub. No.: WO2016/152983
PCT Pub. Date: Sep. 29, 2016

(65) Prior Publication Data
US 2018/0051383 A1    Feb. 22, 2018

(30) Foreign Application Priority Data

Mar. 26, 2015 (JP) ................................ 2015-064067
Mar. 22, 2016 (JP) ................................ 2016-056773

(51) Int. Cl.
| | |
|---|---|
| C23C 18/31 | (2006.01) |
| C23C 18/48 | (2006.01) |
| C25D 3/32 | (2006.01) |
| C25D 3/60 | (2006.01) |
| C07F 9/54 | (2006.01) |
| C25B 11/04 | (2006.01) |

(52) U.S. Cl.
CPC ............. *C25D 3/32* (2013.01); *C07F 9/5442* (2013.01); *C25B 11/0494* (2013.01); *C25D 3/60* (2013.01)

(58) Field of Classification Search
CPC ............. C25D 3/32; C23C 18/31; C23C 18/48
USPC ................................ 106/1.22; 205/302, 303
See application file for complete search history.

(56) References Cited

U.S. PATENT DOCUMENTS

| | | | |
|---|---|---|---|
| 3,778,357 A | 12/1973 | Wolfgang Dahms et al. | |
| 5,147,454 A | 9/1992 | Nishihara et al. | |
| 6,875,260 B2 * | 4/2005 | Verbunt | ............ C23C 18/1653 106/1.11 |
| 2004/0016363 A1 | 1/2004 | Phelps et al. | |
| 2009/0194426 A1 | 8/2009 | Abbott | |
| 2014/0251435 A1 | 9/2014 | Ho et al. | |

FOREIGN PATENT DOCUMENTS

| | | | | |
|---|---|---|---|---|
| CN | 1748044 A | | 3/2006 | |
| EP | 2749672 A2 | | 7/2014 | |
| JP | 48-086741 A | | 11/1973 | |
| JP | 2000128979 A | * | 5/2000 | ............ C08G 65/28 |
| JP | 2001-073153 A | | 3/2001 | |
| JP | 2005-290505 A | | 10/2005 | |
| JP | 2012-087393 A | | 5/2012 | |
| JP | 2013-044001 A | | 3/2013 | |
| RU | SU-1370103 A | * | 1/1998 | ............ C03C 17/06 |

OTHER PUBLICATIONS

International Search Report dated Jun. 7, 2016, issued for PCT/JP2016/059424 and English translation thereof.
Office Action dated Aug. 2, 2018 issued for corresponding Chinese Patent Application No. 201680015498.6.
The extended European search report dated Oct. 24, 2018 issued for corresponding European Patent Application No. 16768886.0.

* cited by examiner

*Primary Examiner* — Edna Wong
(74) *Attorney, Agent, or Firm* — Locke Lord LLP

(57) ABSTRACT

A plating solution including a soluble salt containing at least a stannous salt; an acid selected from organic acid and inorganic acid or a salt thereof; and an additive containing phosphonium salt with two or more of aromatic rings is provided.

4 Claims, No Drawings

PLATING SOLUTION USING PHOSPHONIUM SALT

TECHNICAL FIELD

The present invention relates to a plating solution for tin or a tin alloy which is excellent in uniform electrodepositivity and suppresses generation of voids when a bump electrode is formed.

Priority is claimed on Japanese Patent Application No. 2015-064067, filed Mar. 26, 2015, and Japanese Patent Application No. 2016-056773, filed Mar. 22, 2016, the contents of which are incorporated herein by reference.

BACKGROUND ART

Conventionally, a lead-tin alloy solder plating solution made of an aqueous solution, which contains: at least one selected from an acid and a salt thereof; a soluble lead compound; a soluble tin compound; a nonionic surfactant; and a formalin condensate of naphthalenesulfonic acid or a salt thereof, is disclosed (for example, see Patent Literature 1 (PTL 1)). The plating solution contains, as an additive, the formalin condensate of naphthalenesulfonic acid or the salt thereof in an amount of 0.02 to 1.50 mass % with respect to lead ions. PTL 1 discloses that it is possible to form a lead-tin alloy protruding electrode, which has a small variation in the height of the surface; is smooth; and has a small variation in composition ratio of lead/tin even when plating is performed with this plating solution at a high current density.

In addition, a plating bath of tin or tin alloy, which includes: (A) a soluble salt made of any one of a tin salt and a mixture of a tin salt and a predetermined metal salt of silver, copper, bismuth and lead; (B) an acid or a salt of the acid; and (C) a specific phenanthroline-dione compound, is disclosed (for example, see Patent Literature 2 (PTL 2)). PTL 2 discloses that, by using the plating path, it is possible to have excellent uniform electrodepositivity and film appearance in the wide current density range and to obtain a uniform synthetic composition in the wide current density range.

Furthermore, a tin plating solution, which includes a tin ion source; at least one kind of a nonionic surfactant; and imidazoline-dicarboxylate and 1,10-phenanthroline as additives, is disclosed (for example, see Patent Literature 3 (PTL 3)). PTL 3 discloses that, by using the tin plating solution: there is no burning of plating; and excellent uniformity of the in-plane film thickness distribution is obtained, in plating of a highly-complexed printed board. Moreover, excellent uniformity of through hole plating is obtained.

CITATION LIST

Patent Literature

PTL 1: Japanese Unexamined Patent Application, First Publication No. 2005-290505 (A) (Claim 1, and the paragraph [0004])

PTL 2: Japanese Unexamined Patent Application, First Publication No. 2013-044001 (A) (Abstract, and the paragraph [0010])

PTL 3: Japanese Unexamined Patent Application, First Publication No. 2012-087393 (A) (Abstract, and the paragraph [0006])

SUMMARY OF INVENTION

Technical Problem

The uniform electrodeposition property of the tin or tin alloy plating solution has been improved by the additives described in the above-mentioned PTLs 1 to 3. However, the demand for an improved quality of the plating film is increased; and further improvement of uniform electrodepositivity is needed. In addition, when the bump electrodes, which are provided on a board for connecting a semiconductor device in the flip-chip mounting, are formed by the plating method, empty space called voids are occasionally formed in the inside of the bumps after the reflaw treatment. Since formation of these voids could cause occurrence of contact failure, formation of bumps free of the void is needed. Unfortunately, improving the uniform electrodepositivity and suppressing the occurrence of voids are in conflicting relationships. That is, the uniform electrodepositivity can be improved by increasing the polarization resistance of the electrode surface, while the occurrence of voids is suppressed by reducing the overvoltage of the cathode. In recent years, an additive for a plating solution satisfying both characteristics has been demanded.

The purpose of the present invention is to provide a plating solution for tin or tin alloy which is excellent in uniform electrodepositivity and suppresses occurrence of voids when a bump electrode is formed.

Solution to Problem

The first aspect of the present invention is a plating solution including: (A) a soluble salt containing at least a stannous salt; (B) an acid selected from organic acid and inorganic acid or a salt of the acid; and (C) an additive, wherein the additive includes a phosphonium salt with two or more of aromatic rings represented by a general formula (1) below.

[Chemical formula 1]

(1)

$R_1$ and $R_2$ in the formula (1) are identical or different, and are any one of a phenyl group, a hydrogen atom, $CH_2$—O—$CnH_{2n+1}$, $C_nH_{2n+1}$, n being an integer from 1 to 5, Ph represents a phenyl group, and X represents a halogen.

The second aspect of the present invention is the plating solution according the first aspect of the present invention, wherein the additive further includes a nonionic surfactant represented by a general formula (2) below.

[Chemical formula 2]

$R_3$—$Y_1$—Z—$Y_2$—$R_4$ (2)

In the formula (2), $R_3$ and $R_4$ is the group represented by the formula (A) below; $Y_1$ and $Y_2$ represent a single bond or a group selected from —O—, —COO— and —CONH—; and Z represents a benzene ring or 2,2-diphenylpropane, and in the formula (A), n indicates 2 or 3 and m indicates an integer from 1 to 15.

[Chemical formula 3]

$$—(C_nH_{2n}—O)_m—H \quad (A)$$

The third aspect of the present invention is the plating solution according to the first or second aspect of the present invention, wherein the additive further includes a complexing agent and an antioxidant; or one of a complexing agent and an antioxidant.

Advantageous Effects of Invention

According to the plating solution of the first aspect of the present invention, by using the phosphonium salt as the additive, the uniform electrodepositivity can be improved in the wide current density range; occurrence of the void in formation of the bump electrode can be suppressed; and a plating film, which has a good appearance and is highly reliable, can be formed. As a result, products, which are applicable to a narrow pitch and a complicated wiring pattern at a high quality, can be produced.

According to the plating solution of the second aspect of the present invention, by further including the nonionic surfactant represented by the above-indicated formula (2), occurrence of the void in formation of the bump electrode can be suppressed; and the variation in the thickness of the plating film can be reduced further.

According to the plating solution according to the third aspect of the present invention, by further including the complexing agent and the antioxidant; or one of the complexing agent and the antioxidant, the technical effect explained below can be obtained. That is, the complexing agent: stabilizes the noble metal ions in the bath by the plating solution including noble metal such as silver and the like; and homogenizes the composition of the precipitated alloy. In addition, the antioxidant prevents oxidation of the soluble stannous salt to tin dioxide salt.

DESCRIPTION OF EMBODIMENTS

Next, embodiments for carrying out the present invention are described below.

The plating solution of the first aspect of the present invention (hereinafter referred as "the plating solution of the present invention") is a plating solution for tin or tin alloy, and includes: (A) a soluble salt containing at least a stannous salt; (B) an acid selected from organic acid and inorganic acid or a salt of the acid; and (C) an additive. The additive includes a phosphonium salt with two or more of aromatic rings represented by a general formula (1) below. The soluble salt is made of any one of: the stannous salt; and the mixture of the stannous salt and a metal salt selected from the group consisting of silver, copper, bismuth, nickel, antimony, indium, and zinc.

[Chemical formula 4]

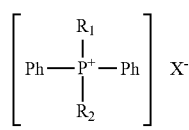

(1)

$R_1$ and $R_2$ in the formula (1) are identical or different, and are any one of a phenyl group, a hydrogen atom, $CH_2—O—CnH_{2n+1}$, $C_nH_{2n+1}$, n being an integer from 1 to 5, Ph represents a phenyl group, and X represents a halogen.

The tin alloy included in the plating solution of the present invention is an alloy of: tin; and a predetermined metal selected from silver, copper, bismuth, nickel, antimony, indium and zinc. Examples thereof include: binary alloys such as the tin-silver alloy, the tin-copper alloy, the tin-bismuth alloy, the tin-nickel alloy, the tin-antimony alloy, the tin-indium alloy, and the tin-zinc alloy; and ternary alloy such as the tin-copper-bismuth, the tin-copper-silver alloy and the like.

Thus, the soluble salt (A) included in the plating solution of the present invention can be any soluble salt that forms varieties of metal ions such as $Sn^{2+}$, $Ag^+$, $Cu^+$, $Cu^{2+}$, $Bi^{3+}$, $Ni^{2+}$, $Sb^{3+}$, $In^{3+}$, $Zn^{2+}$ in the plating solution. For example, it includes: an oxide and a halide of the metal; and a salt formed between an inorganic acid or an organic acid and one of the above-described metals.

Examples of the metal oxide include stannous oxide, copper oxide, nickel oxide, bismuth oxide, antimony oxide, indium oxide, zinc oxide and the like, and examples of the metal halide include stannous chloride, bismuth chloride, bromide Bismuth, cuprous chloride, cupric chloride, nickel chloride, antimony chloride, indium chloride, zinc chloride and the like.

Examples of the metal salt with the inorganic acid or an organic acid include copper sulfate, stannous sulfate, bismuth sulfate, nickel sulfate, antimony sulfate, bismuth nitrate, silver nitrate, copper nitrate, antimony nitrate, indium nitrate, nickel nitrate, zinc nitrate, copper acetate, nickel acetate, nickel carbonate, sodium stannate, stannous fluoroborate, stannous methanesulfonate, silver methanesulfonate, copper methanesulfonate, bismuth methanesulfonate, nickel methanesulfonate, indium metasulfonate, bismethane Zinc sulfonate, stannous ethanesulfonate, bismuth 2-hydroxypropanesulfonate, and the like.

The acid or the salt thereof (B) included in the plating solution of the present invention is selected from organic acid and inorganic acid, or the salt of one of these acids. Examples of the organic acid include: organic sulfonic acids such as alkanesulfonic acid, alkanol sulfonic acid and aromatic sulfonic acid; and aliphatic carboxylic acids. Examples of the inorganic acids include: borofluoric acid, hydrosilicofluoric acid, sulfamic acid, hydrochloric acid, sulfuric acid, nitric acid, perchloric acid and the like. The salt includes: a salt of an alkali metal, a salt of an alkaline earth metal, an ammonium salt, an amine salt, a sulfonate and the like. The component (B) is preferably an organic sulfonic acid from the viewpoint of the solubility of the metal salt and ease of wastewater treatment.

As the alkanesulfonic acid, those represented by the chemical formula $C_nH_{n+1}SO_3H$ (for example, n=1 to 5, preferably 1 to 3) can be used. Specifically, examples thereof include methanesulfonic acid, ethanesulfonic acid, 1-propanesulfonic acid, 2-propanesulfonic acid, 1-butanesulfonic acid, 2-butanesulfonic acid, pentanesulfonic acid and the like, as well as hexanesulfonic acid, decanesulfonic acid, dodecanesulfonic acid and the like.

As the alkanol sulfonic acid, those represented by the chemical formula $C_mH_{2m+1}—CH(OH)—C_pH_{2p}—SO_3H$ (for example, m=0 to 6, p=1 to 5) can be used. Specifically, examples thereof include 2-hydroxyethane-1-sulfonic acid, 2-hydroxypropane-1-sulfonic acid, 2-hydroxybutane-1-sulfonic acid, 2-hydroxypentane-1-sulfonic acid, as well as 1-hydroxypropane-2-sulfonic acid, 3-hydroxypropane-1- sulfonic acid, 4-hydroxybutane-1-sulfonic acid, 2-hydroxyhexane-1-sulfonic acid, 2-hydroxydecane-1-sulfonic acid, 2-hydroxydodecane-1-sulfonic acid and the like.

Basically, the above-mentioned aromatic sulfonic acid is benzenesulfonic acid, alkylbenzenesulfonic acid, phenolsulfonic acid, naphthalenesulfonic acid, alkylnaphthalenesulfonic acid and the like. Specifically, examples thereof include 1-naphthalenesulfonic acid, 2-naphthalenesulfonic acid, toluenesulfonic acid, xylene sulfonic acid, p-phenolsulfonic acid, cresolsulfonic acid, sulfosalicylic acid, nitrobenzene sulfonic acid, sulfobenzoic acid, diphenylamine-4-sulfonic acid and the like.

Examples of the aliphatic carboxylic acid include acetic acid, propionic acid, butyric acid, citric acid, tartaric acid, gluconic acid, sulfosuccinic acid, trifluoroacetic acid and the like.

The phosphonium salt included in the additive (C) included in the plating solution of the present invention is represented by the following general formula (1) as described above.

[Chemical formula 5]

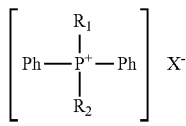

(1)

In the formula (1), $R_1$ and $R_2$ may be identical or different, and these substituents $R_1$ and $R_2$ are selected from:
(a) phenyl group;
(b) a hydrogen atom;
(c) $CH_2$—O—$C_nH_{2n+1}$; (n=1 to 5); and
(d) $C_nH_{2n+1}$; (n=1 to 5).

In the formula (1), Ph represents a phenyl group, and X represents a halogen.

Specific examples of the phosphonium salt included in the plating solution of the present invention are as follows.

(i) The phosphonium salt 1 is tetraphenylphosphonium chloride. In the above formula (1), both substituents $R_1$ and $R_2$ are phenyl groups, and X is chlorine, and is represented by the following formula.

[Chemical formula 6]

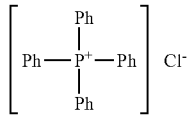

(ii) Phosphonium salt 2 is methoxymethyltriphenylphosphonium chloride. In the above formula (1), the substituent $R_1$ is a phenyl group, $R_2$ is $CH_2$—O—$CH_3$, X is chlorine, and is represented by the following formula.

[Chemical formula 7]

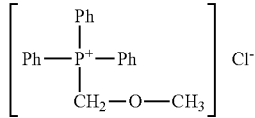

(iii) The phosphonium salt 3 is butoxymethyltriphenylphosphonium bromide. In the above formula (1), the substituent $R_1$ is a phenyl group, $R_2$ is $CH_2$—O—$C_4H_9$, X is bromine and is represented by the following formula.

[Chemical formula 8]

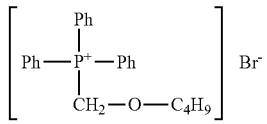

(iv) The phosphonium salt 4 is butyltriphenylphosphonium chloride. In the above formula (1), the substituent $R_1$ is a phenyl group, $R_2$ is $C_4H_9$, X is chlorine, and is represented by the following formula.

[Chemical formula 9]

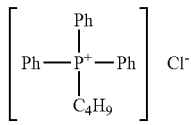

(v) The phosphonium salt 5 is methylpentyldiphenylphosphonium chloride. In the above formula (1), the substituent $R_1$ is $CH_3$, $R_2$ is $C_5H_{11}$, X is chlorine, and is represented by the following formula.

[Chemical formula 10]

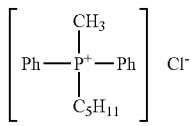

(vi) The phosphonium salt 6 is triphenylphosphonium chloride. In the above formula (1), the substituent $R_1$ is H, $R_2$ is a phenyl group, X is chlorine, and is represented by the following formula.

[Chemical formula 11]

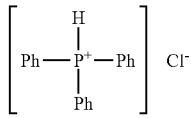

(vii) The phosphonium salt 7 is decyltriphenylphosphonium bromide. In the above formula (1), the substituent $R_1$ is a phenyl group, $R_2$ is $C_{10}H_{21}$, X is bromine, and is represented by the following formula.

[Chemical formula 12]

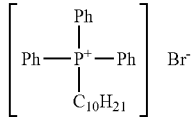

The plating solution of the present invention preferably further includes a nonionic surfactant represented by the following formula (2) as another additive.

[Chemical formula 13]

$$R_3-Y_1-Z-Y_2-R_4 \quad (2)$$

In the formula (2), $R_3$ and $R_4$ are groups represented by the following formula (A). $Y_1$ and $Y_2$ are groups selected from: a single bond; and a group selected from —O—, —COO— and —CONH—. Z represents a benzene ring or 2,2-diphenylpropane. In formula (A), n is 2 or 3. m is an integer of 1 to 15.

[Chemical formula 14]

$$-(C_nH_{2n}-O)_m-H \quad (A)$$

Specific examples of the nonionic surfactant represented by formula (2) included in the plating solution of the present invention are as follows. The nonionic surfactant 1 represented by the formula (2) is polyoxyethylene bisphenol ether. In the above formula (2), the substituent $R_3$ is H—(CH$_2$—CH$_2$—O)$_p$ (p is an integer of 2 to 10), $Y_1$ is —O—, Z is (C$_6$H$_{10}$)C$_3$H$_4$(C$_6$H$_{10}$), $Y_2$ is —O—. $R_4$ is H—(CH$_2$—CH$_2$—O)$_p$ (p is an integer from 2 to 10) and is represented by the following formula.

[Chemical formula 15]

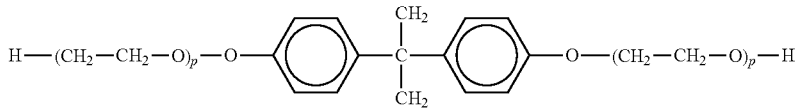

The nonionic surfactant 2 represented by the formula (2) is polyoxyethylene phenyl ether. In the above formula (2), the substituent $R_3$ is H—(CH$_2$—CH$_2$—O)$_q$ (q is an integer of 2 to 15). $Y_1$ is —O—. Z is C$_6$H$_{10}$, $Y_2$ is a single bond, $R_4$ is CH$_2$—CH$_2$—OH, and is represented by the following formula.

[Chemical formula 16]

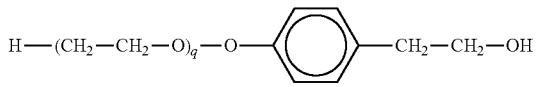

The plating solution of the present invention preferably further includes, as other additives, a surfactant, a complexing agent and/or an antioxidant other than the above.

Other surfactants in this case include ordinary anionic surfactants, cationic surfactants, nonionic surfactants and amphoteric surfactants.

Examples of the anionic surfactant include: polyoxyalkylene alkyl ether sulfates such as polyoxyethylene (containing 12 mol of ethylene oxide) nonyl ether sodium sulfate; polyoxyethylene alkyl ether sulfate such as polyoxyethylene (containing 12 mol of ethylene oxide) dodecylphenyl ether sodium sulfate; alkyl benzene sulfonates such as sodium dodecyl benzene sulfonate, naphthol sulfonates such as sodium 1-naphthol-4-sulfonate and disodium 2-naphthol-3,6-disulfonate; naphthol sulfonate salts such as sodium 1-naphthol-4-sulfonate and disodium 2-naphthol-3,6-disulfonate; (poly) alkylnaphthalenesulfonic acid salts such as sodium diisopropylnaphthalenesulfonate and sodium dibutylnaphthalenesulfonate; alkyl sulfates such as sodium dodecyl sulfate and sodium oleyl sulfate; and the like.

Examples of the cationic surfactant include mono to tri alkylamine salts, dimethyldialkylammonium salt, trimethylalkylammonium salt, dodecyltrimethylammonium salt, hexadecyltrimethylammonium salt, octadecyltrimethylammonium salt, dodecyldimethylammonium salt, octadecenyl Dimethyl ethyl ammonium salt, dodecyl dimethyl benzyl ammonium salt, hexadecyl dimethyl benzyl ammonium salt, octadecyl dimethyl benzyl ammonium salt, trimethyl benzyl ammonium salt, triethyl benzyl ammonium salt, hexadecyl pyridinium salt, dodecyl pyridinium salt, dodecyl picolinium salt, dodecylimidazolinium salt, oleyl imidazolinium salt, octadecylamine acetate, dodecylamine acetate, and the like.

Examples of the nonionic surfactant include, a sugar ester, fatty acid ester, C1 to C25 alkoxyl phosphate (salt), sorbitan ester, C1 to C22 aliphatic amide and the like, to which 2 to 300 moles of ethylene oxide (EO) and/or propylene oxide (PO) are additionally condensed. In addition, examples of the nonionic surfactant include the sulfuric acid adduct or the sulfonate adduct of a condensation product of: silicon-based polyoxyethylene ether, silicon-based polyoxyethylene ester, fluorine-based polyoxyethylene ether, fluorine-based polyoxyethylene ester, ethylene oxide and/or propylene oxide; and alkylamine or diamine.

Examples of the amphoteric surfactant include betaine, carboxybetaine, imidazolinium betaine, sulfobetaine, aminocarboxylic acid and the like.

The above-described complexing agent is used for stabilizing noble metal ions and the like in the bath with the plating solution including a noble metal such as silver and homogenizing the composition of the precipitated alloy. Examples of the complexing agent include oxycarboxylic acid, polycarboxylic acid, monocarboxylic acid and the like. Specific examples include gluconic acid, citric acid, glucoheptonic acid, gluconolactone, glucoheptolactone, formic acid, acetic acid, propionic acid, butyric acid, ascorbic acid, oxalic acid, malonic acid, succinic acid, glycolic acid, malic acid, Tartaric acid, diglycolic acid, thioglycolic acid, thiodiglycolic acid, thioglycol, thiodiglycol, mercaptosuccinic acid, 3,6-dithia-1,8-octanediol, 3,6,9-trithiadecane-1,11-disulfonic acid, thiobis (dodecaethylene glycol), di(6-methylbenzothiazolyl) disulfide trisulfonic acid, di(6-chlorobenzothiazolyl) disulfide disulfonic acid, gluconic acid, citric acid, glucoheptonic acid, gluconolactone, glucoheptolactone, dithiodianiline, dipyridyl disulfide, mercaptosuccinic acid, sulfite, thiosulfate, ethylenediamine, ethylenediamine tetraacetic acid (EDTA), diethylenetriaminepentaacetic acid (DTPA), nitrilotriacetic acid (NTA), iminodiacetic acid (IDA), iminodipropionic acid (IDP), hydroxyethyl ethylenediamine triacetic acid (HEDTA), triethylenetetramine hexaacetic acid (TTHA), ethylenedioxybis (ethylamine)-N, N,N',N'-tetraacetic acid, glycine, nitrilotrimethylphosphonic acid or salts thereof and the like. They also include sulfur-containing compounds such as thioureas and phosphorus compounds such as tris (3-hydroxypropyl) phosphine. Examples of the conductive salt include sodium salt, potassium salt, magnesium salt, ammonium salt, amine salt and the like of sulfuric acid, hydrochloric acid, phosphoric acid, sulfamic acid, sulfonic acid.

The antioxidant is used to prevent oxidation of soluble stannous salt to tin dioxide salt. Examples of the antioxidant include hypophosphorous acids, ascorbic acid or the salts thereof, phenol sulfonic acid (Na), cresolsulfonic acid (Na), hydroquinone sulfonic acid (Na), hydroquinone, α or β-naphthol, catechol, resorcinol, phloroglucin, hydrazine, phenolsulfonic acid, catecholsulfonic acid, hydroxybenzenesulfonic acid, naphtholsulfonic acid, the salts thereof, and the like.

The phosphonium salt (C) included in the plating solution of the present invention can be used singly or in combination, and the content in the plating solution is 0.1 to 10 g/L, preferably 0.5 to 5 g/L. If the content is less than the appropriate range, uniform electrodepositivity and effect of improving the film appearance cannot be obtained sufficiently, whereas if it is too much, burning of plating may occur.

The predetermined soluble metal salt (A) can be used singly or in combination, and the content thereof in the plating solution is 30 to 100 g/L, preferably 40 to 60 g/L. When the content is less than the appropriate range, productivity drops. As the content increases, the cost of the plating solution increases.

The inorganic acid, the organic acid or the salt thereof (B) can be used singly or in combination, and the content thereof in the plating solution is 80 to 300 g/L, preferably 100 to 200 g/L. If the content is less than the appropriate range, the conductivity decreases; and the voltage increases. When the content increases, the viscosity of the plating solution rises and the agitation speed of the plating solution decreases.

The additive concentrations of the above-described components (A) to (C) are arbitrarily adjusted/selected according to the plating method such as barrel plating, rack plating, high-speed continuous plating, rackless plating, bump plating and the like.

On the other hand, the liquid temperature of the electroplating solution of the present invention is generally 70° C. or less, preferably 10 to 40° C. The cathode current density is generally 0.01 to 150 A/dm$^2$, preferably 0.1 to 100 A/dm$^2$. When the current density is too low, the productivity deteriorates, whereas when it is too high, the uniform electrodepositivity deteriorates.

A predetermined metal film can be formed on an electronic component by applying the plating solution of tin or tin alloy containing the phosphonium salt included in the plating solution of the present invention to the electronic component to be plated. Examples of the electronic parts include a printed circuit board, a flexible printed circuit board, a film carrier, a semiconductor integrated circuit, a resistor, a capacitor, a filter, an inductor, a thermistor, a quartz oscillator, a switch, a lead wire, and the like. In addition, it is also possible to form a film by applying the plating solution of the present invention to a part of an electronic part such as a bump electrode of a wafer.

EXAMPLES

[Phosphonium Salt Used in Examples 1 to 8 and Comparative Example 2]

Among Examples 1 to 8 of the present invention, Example 1 is an example of a tin plating solution including the phosphonium salt 1; Example 2 is an example of a tin-silver alloy plating solution including the phosphonium salt 1, Example 3 is an example of a tin-silver alloy plating solution including the phosphonium salt 2; Example 4 is an example of a tin plating solution including the phosphonium salt 3; Example 5 is an example of a tin-copper alloy plating solution including the phosphonium salt 4; and Example 6 is an example of a tin-silver alloy plating solution including the phosphonium salt 5. Example 7 is an example of a tin-bismuth alloy plating solution including the phosphonium salt 6; and Example 8 is an example of a tin-zinc alloy plating solution including the phosphonium salt 5. Among Comparative Examples 1 and 2, Comparative Example 1 is an example of the tin plating solution not including the phosphonium salt; and Comparative Example 2 is an example of the tin-silver alloy plating solution including the phosphonium salt 7. Examples 1 and 4 of the present invention and Comparative Example 1 were acidic tin plating solutions, Examples 2 to 3 and 5 to 8 of the present invention and Comparative Example 2 were acidic tin alloy plating solutions.

The phosphonium salts 1 to 6 of Examples 1 to 8 of the present invention and the phosphonium salt 7 of Comparative Example 2 can be purchased from chemical manufacturers. Details of the phosphonium salt used in Examples 1 to 8 of the present invention and Comparative Example 2 are shown in Table 1.

TABLE 1

| Kind of the phosphonium salt | (C) Additive represented by the general formula (1) | | |
|---|---|---|---|
| | $R_1$ | $R_2$ | X |
| Phosphonium salt 1 | Ph | Ph | Cl |
| Phosphonium salt 2 | Ph | $CH_2$—O—$CH_3$ | Cl |
| Phosphonium salt 3 | Ph | $CH_2$—O—$C_4H_9$ | Br |
| Phosphonium salt 4 | Ph | $C_4H_9$ | Cl |
| Phosphonium salt 5 | $CH_3$ | $C_5H_{11}$ | Cl |
| Phosphonium salt 6 | H | Ph | Cl |
| Phosphonium salt 7 | Ph | $C_{10}H_{21}$ | Br |

Examples 1 to 8 and Comparative Examples 1 and 2

Examples 1 to 8 of the present invention and Comparative Examples 1 and 2 in which the components (A) to (C) and various combinations of surfactants, complexing agents and antioxidants were changed are shown in Tables 2 and 3. In Table 3, "surfactant 1" means polyoxyethylene bisphenol ether and "surfactant 2" means polyoxyethylene phenyl ether, respectively.

TABLE 2

| | (A) | | (B) | | (C) | |
|---|---|---|---|---|---|---|
| | Substance name | Concentration g/L | Substance name | Concentration g/L | Substance name | Concentration g/L |
| Example 1 | Methanesulfonate Sn | 50 | Methanesulfonic acid | 120 | Phosphonium salt 1 | 3 |
| Example 2 | Methanesulfonate Sn<br>Methanesulfonate Ag | 50<br>1 | Methanesulfonic acid | 120 | Phosphonium salt 1 | 0.5 |
| Example 3 | Methanesulfonate Sn<br>Methanesulfonate Ag | 50<br>1 | Methanesulfonic acid | 120 | Phosphonium salt 2 | 7 |
| Example 4 | Sulfate Sn | 50 | Sulfuric acid | 120 | Phosphonium salt 3 | 0.5 |
| Example 5 | Methanesulfonate Sn<br>Methanesulfonate Cu | 50<br>1 | Methanesulfonic acid | 120 | Phosphonium salt 4 | 1 |
| Example 6 | Methanesulfonate Sn<br>Methanesulfonate Ag | 50<br>1 | Methanesulfonic acid | 120 | Phosphonium salt 5 | 5 |
| Example 7 | Phenolsulfonate Sn<br>Phenolsulfonate Bi | 50<br>1 | Phenolsulfonic acid | 120 | Phosphonium salt 6 | 1 |
| Example 8 | Methanesulfonate Sn<br>Methanesulfonate Zn | 50<br>1 | Methanesulfonic acid | 120 | Phosphonium salt 5 | 5 |
| Comparative Example 1 | Methanesulfate Sn | 50 | Methanesulfonic acid | 120 | — | — |
| Comparative Example 2 | Methanesulfonate Sn<br>Methanesulfonate Ag | 50<br>1 | Methanesulfonic acid | 120 | Phosphonium salt 7 | 0.5 |

TABLE 3

| | Other additives | | | | | |
|---|---|---|---|---|---|---|
| | Nonionic surfactant | Concentration g/L | Complexing agent | Concentration g/L | Antioxidant | Concentration g/L |
| Example 1 | Surfactant 1 | 5 | — | — | Catechol | 1 |
| Example 2 | Surfactant 1 | 5 | Thiourea | 10 | Catechol | 1 |
| Example 3 | Surfactant 1 | 5 | Thiourea | 10 | Catechol | 1 |
| Example 4 | Surfactant 2 | 5 | — | — | Hydroquinone | 1 |
| Example 5 | Surfactant 2 | 5 | Thioglycol | 10 | Hydroquinone | 1 |
| Example 6 | Surfactant 2 | 5 | Thioglycol | 10 | Hydroquinone | 1 |
| Example 7 | Surfactant 2 | 5 | Thioglycol | 10 | Hydroquinone | 1 |
| Example 8 | Surfactant 2 | 5 | Thioglycol | 10 | Hydroquinone | 1 |
| Comparative Example 1 | Surfactant 1 | 5 | — | — | Catechol | 1 |
| Comparative Example 2 | Surfactant 2 | 5 | Thiourea | 10 | Hydroquinone | 1 |

[Evaluation Test]

With respect to the plating solutions obtained in Examples 1 to 8 of the present invention and Comparative Examples 1 and 2, a Hull cell test and a plating test were conducted, and the electrodepositivity of each plating solution was evaluated. The results are shown in Table 4.

(A) Hull Cell Test

In the Hull cell test, a commercially available Hull cell tester (manufactured by Yamamoto Plating Test Instrument Co., Ltd.) was used, and a copper hulled cell plate (length 70 mm, width 100 mm, thickness 0.3 mm) was used as a substrate to be plated. The plating solution was placed in a Hull cell tester, the liquid temperature was set to 25° C., and the energizing current was 2 A. The plating time was 5 minutes and the plating solution was not stirred during the plating process. The hull cell evaluation was made according to the presence or absence of burning of plating on the plated hull cell plate.

(B) Plating Test (B-1) Variation in Plating Film Thickness

In the first plating test, a copper substrate (10 cm in length, 10 cm in width, 0.3 mm in thickness) was immersed in a plating solution at a liquid temperature of 25° C. and subjected to a current density of 5 A/dm$^2$ for 1 minute. The film thickness of 10 places of the obtained plating film was measured with a fluorescent X-ray film thickness measuring device (manufactured by SII NanoTechnology Inc.). The standard deviation (3σ) of the film thickness at ten places was calculated, and it was evaluated whether the plating film thickness variation, that is, the electrodeposition was performed uniformly.

(B-2) Void Occurrence Rate of Plating Film

In the second plating test, a copper substrate (10 cm in length, 7 cm in width, 0.3 mm in thickness) was immersed in a plating solution at a liquid temperature of 25° C. and energized at a current density of 3 A/dm$^2$ for 13 minutes to form a plating film on the substrate. The center of the substrate with the plating film was cut into square pieces of 10 mm in length and 10 mm in width. Simulating the reflaw treatment, these pieces were heated in a nitrogen atmosphere with a hot plate until the surface temperature of the substrate reached 270° C., and then rapidly cooled after retaining them at the raised temperature for 10 seconds. Evaluation of voids was conducted by: observing the plating film after reflow with transmission X-ray; and calculating the void area ratio by dividing the area occupied by the void by the area of the small pieces of 10 mm in length and 10 mm in width. The presence or absence of the voids was evaluated based on the above-described void area ratio, and when the void area ratio was 0.1% or more, it was defined as "voids were generated."

TABLE 4

|  | Hull cell test | Plating test | |
| --- | --- | --- | --- |
|  | Presence or absence of burning of plating | Standard deviation of the plating film thickness (3σ) | Void area ratio (%) |
| Example 1 | Absent | 0.76 | 0.03 |
| Example 2 | Absent | 0.65 | 0.02 |
| Example 3 | Absent | 0.46 | 0.04 |
| Example 4 | Absent | 0.45 | 0.01 |
| Example 5 | Absent | 0.62 | 0.01 |
| Example 6 | Absent | 0.88 | 0.07 |
| Example 7 | Absent | 0.51 | 0.06 |
| Example 8 | Absent | 0.59 | 0.04 |
| Comparative Example 1 | Present | 1.93 | 0.08 |
| Comparative Example 2 | Present | 0.89 | 5.7 |

[Result of Evaluation]

As is apparent from Table 4, in Comparative Example 1 in which plating was performed with the tin plating solution not including a phosphonium salt, the variation in plating film thickness was as large as 1.93. In Comparative Example 2 in which the plating was performed with the tin plating solution including $R_2$ having the formula (1) represented by $C_{10}H_{21}$, since n of $CnH_{2n+1}$ was 10, the void area ratio was as large as 5.7%. On the other hand, in Examples 1 to 8 of the present invention in which plating was carried out with the tin plating solution including phosphonium salts satisfying the prescribed conditions of $R_1$ and $R_2$ in the formula (1), the variation of the plating film thickness was as low as 0.45 to 0.88. In Examples 1 to 8 of the present invention, the void area ratio was as low as 0.01 to 0.07. Thus, it was demonstrated that a good plating film was obtained with an excellent uniform electrodepositivity free of void generation.

INDUSTRIAL APPLICABILITY

The plating solution of the present invention can be applied to electronic components such as printed boards, flexible printed boards, film carriers, semiconductor integrated circuits, resistors, capacitors, filters, inductors, thermistors, crystal resonators, switches, lead wires and the like; and a part of electronic component such as the bump electrode of the wafer.

What is claimed is:

1. A plating solution comprising:
   (A) a soluble salt containing at least a stannous salt in an amount of 30 to 100 g/L;
   (B) an acid selected from an organic acid and an inorganic acid, or a salt of the acid, in an amount of 80 to 300 g/L; and
   (C) an additive, wherein
   the additive comprises a phosphonium salt in an amount of 0.1 to 10 g/L, the phosphonium salt having two or more of aromatic rings represented by a general formula (1) below,

(1)

wherein, $R_1$ and $R_2$ in the formula (1) are identical or different, and are any one of a phenyl group, a hydrogen atom, $CH_2-O-C_nH_{2n+1}$, $C_nH_{2n+1}$, n being an integer from 1 to 5,
Ph represents a phenyl group, and
X represents a halogen.

2. The plating solution according to claim 1, wherein the additive further comprises a nonionic surfactant represented by a general formula (2) below, $$R_3-Y_1-Z-Y_2-R_4 \quad (2)$$

and wherein, in the formula (2), $R_3$ and $R_4$ is represented by the formula (A) below, $$-(C_nH_{2n}-O)_m-H \quad (A)$$

and wherein, $Y_1$ and $Y_2$ represent a single bond or a group selected from —O—, —COO— and —CONH—; and Z represents a benzene ring or 2,2-diphenylpropane, and
in the formula (A), n indicates 2 or 3 and m indicates an integer from 1 to 15.

3. The plating solution according to claim 2, wherein the additive further comprises a complexing agent and an antioxidant; or one of a complexing agent and an antioxidant.

4. The plating solution according to claim 1, wherein the additive further comprises a complexing agent and an antioxidant; or one of a complexing agent and an antioxidant.

* * * * *